United States Patent [19]

Ohe

[11] Patent Number: 4,986,657

[45] Date of Patent: Jan. 22, 1991

[54] APPARATUS FOR ANALYZING PARTICLES USING SCATTERED AND FLUORESCENT LIGHT

[75] Inventor: Shinichi Ohe, Yokohama, Japan

[73] Assignee: Canon Kabushiki Kaisha, Tokyo, Japan

[21] Appl. No.: 221,596

[22] Filed: Jul. 20, 1988

[30] Foreign Application Priority Data

Jul. 31, 1987 [JP] Japan .................................. 62-192203

[51] Int. Cl.$^5$ ...................... G01N 15/14; G01N 21/64
[52] U.S. Cl. .................................... 356/73; 250/222.2; 328/116; 356/336; 356/338
[58] Field of Search ................... 356/72, 73, 336, 338, 356/339, 343; 250/222.2; 324/71.4; 307/351, 354, 362; 328/115, 116, 117

[56] References Cited

U.S. PATENT DOCUMENTS

| | | | |
|---|---|---|---|
| 4,263,508 | 4/1981 | Leary et al. | ..................... 356/335 X |
| 4,767,997 | 8/1988 | Nielsen | ........................... 328/116 X |

Primary Examiner—Vincent P. McGraw
Attorney, Agent, or Firm—Fitzpatrick, Cella, Harper & Scinto

[57] ABSTRACT

Disclosed is an apparatus for analyzing fine particles such as blood cells in a fluid such as blood, the apparatus comprising a device for generating electrical signal pulses from the specimen particles which have passed a detecting section such as, for example, a flow pass. The signal pulses are compared with a predetermined threshold, and specific information concerning the specimen particles is detected for a period which is determined on the basis of the signals produced by delaying the signal pulses, from a moment at which the threshold value is exceeded by each signal pulse.

9 Claims, 2 Drawing Sheets

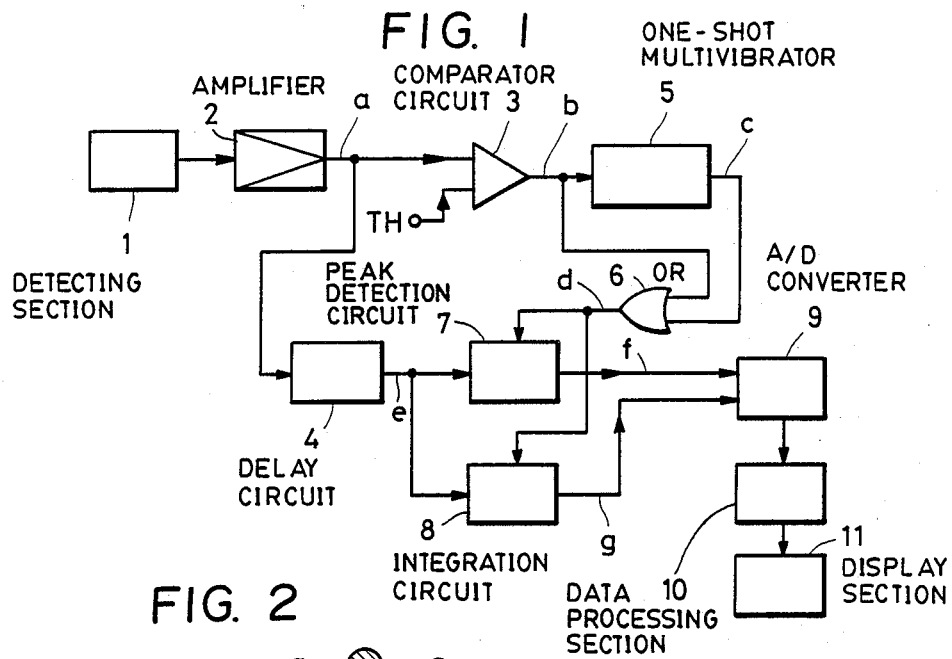
FIG. 1
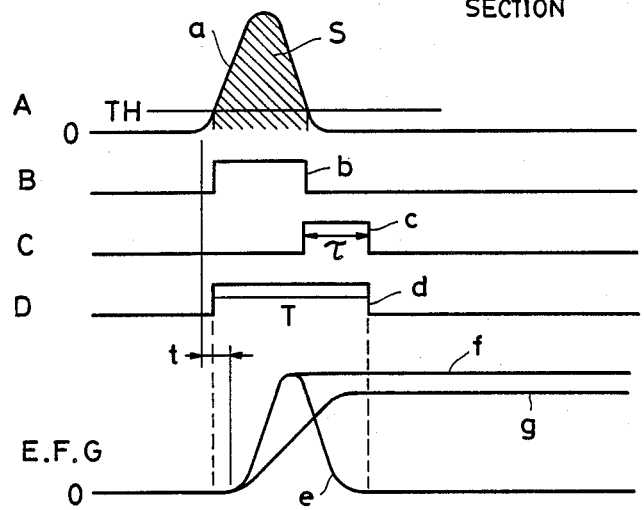
FIG. 2
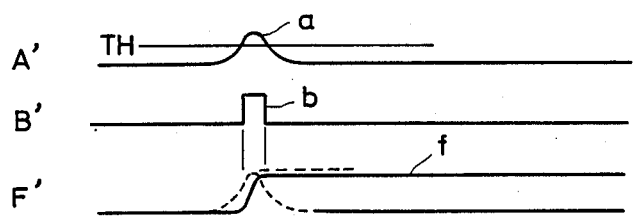

APPARATUS FOR ANALYZING PARTICLES USING SCATTERED AND FLUORESCENT LIGHT

BACKGROUND OF THE INVENTION

1. Field of the Invention

The present invention relates to apparatus and methods for analyzing particles in a fluid and, more particularly, to apparatus and methods for counting and analyzing fine particles such as blood cells in a fluid such as blood through detection of a change in electrical and optical characteristics of the fluid.

2. Description of the Related Art

Apparatus has been known such as a Flow Cytometer as disclosed in the specification of U.S. Pat. No. 4,263,508, in which a specimen liquid suspending fine particles flowing through a restricted passage of very small cross-section in the center of a flow cell is irradiated with a laser beam so as that the nature, construction and other properties of the particles are known from, for example, information available from the signal pulses of the scattered light or fluorescent light from the particles, e.g., peak values of the pulses or integrated values of the pulses. The specification of U.S. Pat. No. 2,656,508 also discloses a counting apparatus for counting blood cells in blood. In this apparatus, the sizes of various kinds of blood cells are measured and the quantity of the blood cells are ascertained through measurement of changes in the electrical impedance of the blood, particularly through measurement of the peak level of signal pulses generated when the blood cells suspended in a suspension liquid pass through a fine passage while being irradiated from a laser beam.

The signals obtained when the specimen particles move across a laser beam or through a minute passage are in the form of electrical pulses. In the known analyzing apparatus, the analysis is conducted by measuring the peak level or the integrated value of these electrical pulse signals.

In these known particle analyzing apparatus, the signal pulses are directly input to peak detection circuit or to an integration circuit and the peak detection circuit or the integration circuit is directly operated in accordance with timing pulses which are produced as a result of comparison between the signal pulses with a predetermined reference level. More specifically, the pulse signal is picked up only when the level thereof exceeds a reference level, and only then is it used to charge capacitors in the peak detection circuit or the integration circuit. In this method, therefore, the period of capacitor charge is shorter than the period corresponding to the actual width of the signal pulses, so that the resulting integration value inevitably involves error in that the value becomes smaller than the value which corresponds to the integration over the actual pulse width. The peak detection circuit also encounters a problem in that the response of this circuit tends to be delayed particularly when the width of the signal pulse is extremely small or when the level of the peak is very small, with the result that a considerable error is involved in the peak level as measured.

SUMMARY OF THE INVENTION

Accordingly, an object of the present invention is to provide an apparatus and a method of analyzing particles in a fluid, in which signal pulses input to the peak detection circuit or to the integration circuit are delayed with respect to the timing of input of the signal pulses to a threshold comparator, thereby enabling the peak level or the integration value to be detected with reduced error.

According to one aspect of the invention, there is provided an apparatus for analyzing particles in a fluid which comprises passage means, pulse generating means, comparator means, delaying means and detection means. The passage means is constructed to cause specimen particles to pass through a detection section. The pulse generating means is constructed to cause specimen particles to pass through a detecting section. The pulse generating means is constructed to produce electrical signal pulses from the specimen particles which have passes through the detecting section. The comparator means is constructed to compare the level of the signal pulses with a predetermined threshold level. The delaying means is arranged to delay the signal pulses and the detection means is arranged to detect specific particle information represented by the delayed signal pulses. The detection means is constructed to perform such detecting from moments at which the threshold level is exceeded by the signal pulses.

According to another aspect of the invention, there is provided a method for analyzing particles in a fluid comprising the steps of causing specimen particles to pass through a detecting section, producing electrical signal pulses corresponding to predetermined characteristics of the specimen particles, comparing the level of the signal pulses with a predetermined threshold level, delaying the signal pulses and detecting specific particle information, represented by the delayed signal pulses, from the moments at which the threshold level has been exceeded by respective signal pulses.

BRIEF DESCRIPTION OF THE DRAWINGS

FIG. 1 is a block diagram of an apparatus embodying the present invention for analyzing particles in a fluid;

FIG. 2 is a waveform chart showing the waveforms of outputs from the apparatus of FIG. 1.

DESCRIPTION OF THE PREFERRED EMBODIMENT

Figure 3:
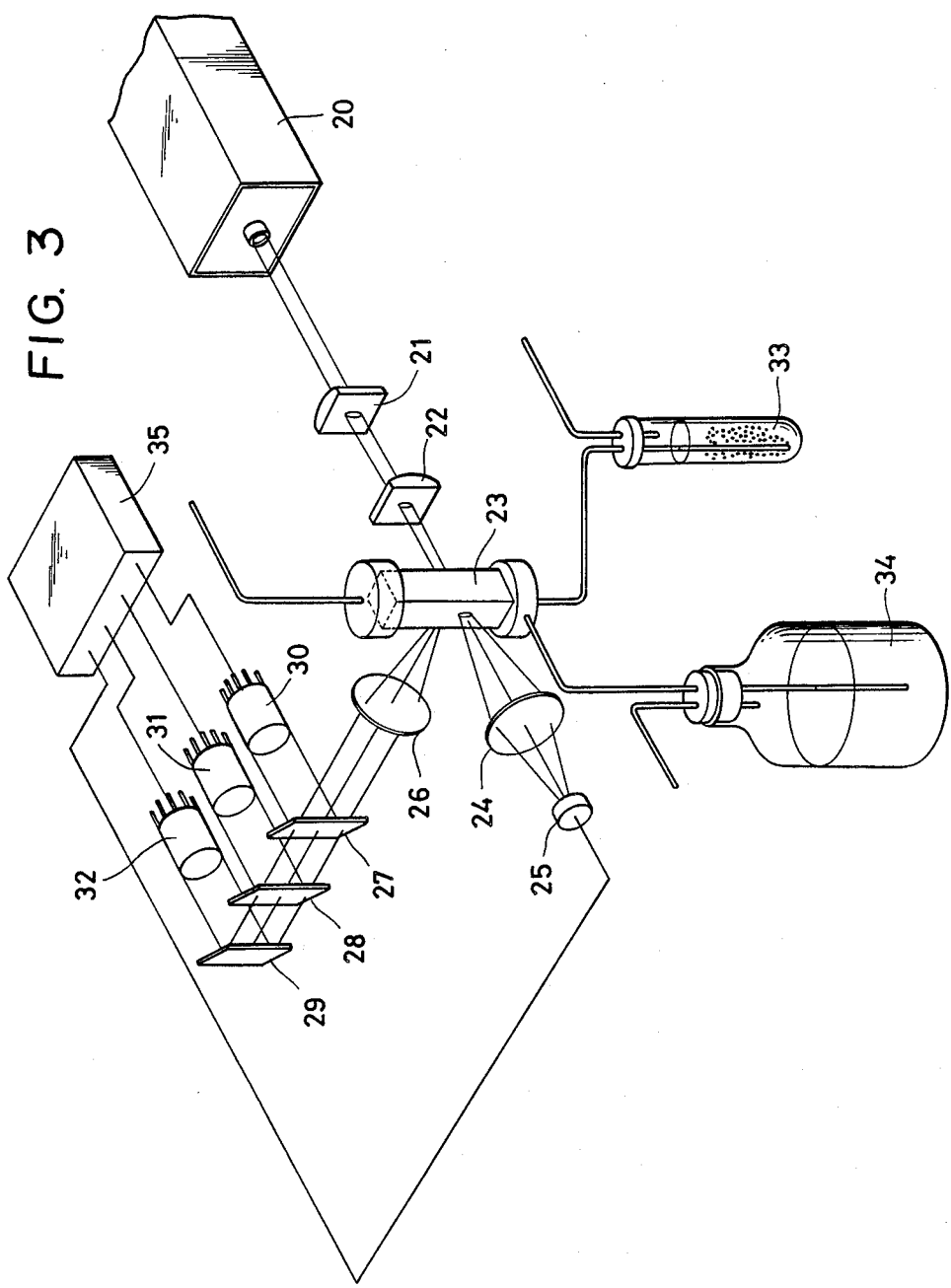
FIG. 3 is a perspective view illustrating the overall construction of an analyzing apparatus incorporating the present invention.

FIG. 3 is an illustration of the overall construction of a particle analyzing apparatus incorporating the present invention. The apparatus includes a sample liquid container 33 containing a sample liquid to which a specimen has been added, and a suspension liquid container 34 containing distilled water which serves as a suspension liquid. The sample liquid is suspended by the suspension liquid which in turn is contracted into a stream of a small diameter which passes substantially through the center of a restricted passage in a flow cell 23. In consequence, the specimen particles are separated so that specimen particles flow individually, one-by-one, through the restricted passage. The apparatus further has a laser source 20 for emitting a laser beam. The laser beam is converted into a beam of a desired cross-section through cylindrical lenses 21, 22 and is applied to the restricted flow of the specimen particles. The applied beam has an oval cross-section having a longitudinal axis extending laterally with respect to the flow of the liquid, so that the specimen particles can receive a uniform intensity of irradiation even if the position of flow of sample liquid is changed.

The specimen particles generate scattered light when irradiated with the beam. The specimen particles also produce fluorescent light when they are dyed with a fluorescent dye for the purpose of fluorescent measurement. Amongst various components of the scattered light, the forward components which are directed forwardly of the laser source 20 are measured by a photodetector 25 through a condenser lens 24. In order to present the emitted beam from directly impinging upon the photo-detector 25, a stopper (not shown) is provided in the path of beam ahead of the condenser lens 24, thus eliminating any component of beam which may otherwise directly reach the photo-detector 25. On the other hand, lateral components of the scattered light are converged through a condenser lens 26 and are reflected in part by a dichroic mirror 27 so as to be measured by a photo-detector 30. In most cases, the lateral scattered light components are measured in the direction orthogonal to the original light path as in the case of the illustrated embodiment, although the measurement may be conducted in some other specific direction such as 45° or 60° with respect to the light path. When the sample liquid is dyes with fluorescent dye, fluorescent light of a very small intensity is generated together with the scattered light. The green component of the fluorescent light is reflected by a dichroic mirror 28 and detected by a photo-sensor 31, while the red component is reflected by a total reflection mirror 29 and detected by a photo-detector 32. Although not shown in the drawings, band-pass filters capable of passing only the light of the respective wavelengths are disposed on the incident side of the photo-detectors. The signals from the photo-detectors 25, 30, 31 and 32 are input to a computing circuit 35 which performs computations necessary for the particle analysis.

A description will be made hereinunder as to the construction of a computing circuit 35, with reference to FIGS. 1 and 2.

Referring to FIG. 1, a reference numeral 1 denotes a detecting section composed of a photo-detector 25. The output from the detecting section is amplified by an amplifier 2, the output of which is branched into two branches: namely, a branch connected to a comparator circuit 3 and a branch connected to a delay circuit 4. The comparator circuit 3 also receives a reference or threshold level signal TH. The output from the comparator circuit 3 also is directly connected to the OR circuit. The output from the OR circuit 6 is branched into two branches, one which is connected to a peak detection circuit 7, while the other is connected to an integration circuit 8. Although not shown, the outputs from each of the respective photo-detectors 30, 31 and 32 are input to respective peak detection and integration circuits through amplifiers and delay circuits, each having the same construction as the circuits denoted by 2, 4, 7 and 8. Thus, there are eight outputs derived from the several integration circuit 8. These eight outputs are connected to an A/D converter 9 the output of which is input to a display section 11 through a data processing section 10. Optical signal pulses which are obtained when the specimen particles move across the laser beam are detected by the detecting sectional and are input to the amplifier 2. The output signal pluses a from the amplifier have waveforms as shown in waveform A of FIG. 2. The signal pulses a are then input to the comparator circuit 3 so as to be compared with the threshold level signal TH, whereby timing pulses b are obtained as illustrated in waveform B of FIG. 2.

In the conventional method, the integration circuit 8 are operated in this period so that the charge capacitors in the integration circuit 8 are charged only during the periods of the timing pulses. Thus, the conventional method allows only the hatched area S of each pulse to be stored, so that only a value proportional to the hatched area S can be obtained as the integrated value. Thus, both wing portions of each pulse a are omitted from the integration, so as to incur an error. The error value is increased as the pulse peak level becomes lower. As shown in A' in FIG. 2, the rise of the pulse at the threshold level is very steep when the pulse peak level is very low or when the pulse width is small. Thus, the timing pulse output from the comparator circuit 3, which represents the charging period for charging the capacitor of the peak detection circuit 7 is very short, as shown by B' in FIG. 2. Consequently, the output f from the peak detection circuit 7 cannot precisely follow the signal pulse a, with the result that the measured value of the peak level contains an error.

In order to solve this problem, in this embodiment, the signal pulse e input to the peak detection circuit 7 or to the integration circuit 8 is delayed by a predetermined time length t, as shown by the waveform E in FIG. 2, by being passed through a delay circuit 4. The peak detection circuit 7 or the integration circuit 8 are operated in accordance with the pulses d which are obtained as the OR combination of the output pulse b from the comparator circuit 3 and a pulse c which lasts from the moment of fall of the pulse b for a time length longer than the time t shown in C of FIG. 2. Thus, the charge capacitor of the peak detection circuit 7 or the integration circuit 8 is charged for a period T represented by the width of the pulse d. Similarly, the output signals from each of the photo-detectors 30 to 32 are made to pass through delay circuits so as to be used in accordance with the above-mentioned pulse d.

With this arrangement, the integration circuit 8 can commence its operation even in the beginning portion of the period of the signal pulse e in which pulse slope is gentle. Similarly, the trailing end portion of the pulse also is contained in the integration so that the integrated value q is obtained with reduced error as shown in FIG. 2G. It is also to be understood that the peak detection circuit 7 also commences its operation from the beginning period of the pulse in which the slope is still gentle, so that it can closely follow the signal pulse e, whereby the peak value f can be obtained without error as shown in FIG. 2F. Both or either one of the outputs f and g from the peak detection circuit 7 and the integration circuit 8 are delivered in the form of voltage signal to an A/D (analog to digital) converter 9 so as to be converted into digital signals which are then input to a data processing section 10. The data processing section 10 conducts a statistical processing, e.g., to produce a histogram based on the input digital values, and the result is output to a display section 11.

In the described embodiment, the peak detection circuit 7 and the integration circuit 8 are operated in the period which is obtained as the OR combination of the output b from the comparator circuit 3 and the output c from the one-shot multivibrator circuit 5 obtained from the fall of the output b. This, however, is only illustrative and the arrangement may be such that the output of the comparator circuit 3 is made to pass through a delay circuit 4 in place of the one-shot multi-vibrator circuit 5 so that the peak detection circuit 7 is made to operate during a period which corresponds to the OR combination of the output b from the comparator circuit 3 and a signal obtained by delaying the output b.

It is also to be noted that, although the logic circuit can operate on the basis of the output from only the photodetector 25, the logic circuit may employ the output from any one of the other photo-detectors 30 to 32. It is also possible to form the final pulse d by a suitable combination such as OR and AND of the logical outputs from these photo-detectors 30 to 32.

It is also to be noted that the invention can be realized by using pulses such as those produced as a result of the electrical impedance changes which are caused when the specimen particles pass through a fine passageway, even though the illustrated embodiment makes use of the light signal pulses obtained from the specimen particles themselves.

The various elements designated by the boxes in FIGS. 1 and 3 are per se well known and no special construction of any of these elements is needed to carry out the invention according to the best mode contemplated by the inventor.

What is claimed is:

1. An apparatus for analyzing particles, comprising:
   irradiation means for irradiating particles in a detecting section;
   first receiving means for receiving and photoelectrically converting scattered light from said detecting section, and second receiving means for receiving and photoelectrically converting fluorescent light generated concurrently with said scattered light;
   comparator means connected to said first receiving means for comparing a level of signal pulses of said scattered light with a predetermined threshold level and for generating timing pulses from moments at which said signal pulses exceed said threshold level;
   pulse generating means connected to said comparator means for generating gate pulses by adding a predetermined period to said timing pulses;
   delaying means connected to said first and second receiving means for delaying a photoelectrically converted detecting signal of each of said scattered light and fluorescent light and for generating from each a delayed signal pulse;
   measuring means for measuring values, by a selected one of integrating and peak-holding, of each delayed signal pulse outputted from said delaying means during the period of said gate pulses; and
   analyzing means for analyzing the particles using the measured values of said scattered light and fluorescent light measured by said measuring means.

2. An apparatus according to claim 1, wherein said first receiving means separately receives forward scattered light.

3. An apparatus according to claim 1, wherein said second receiving means comprises plural light detectors for receiving fluorescent light of plural colors, respectively.

4. An apparatus according to claim 1, wherein said detecting section is a flow passage in a flow cell and each particle passes one by one through the detecting section.

5. An apparatus according to claim 1, wherein said irradiation means comprises a laser source.

6. An apparatus for analyzing particles comprising:
   irradiation means for irradiating particles in a detecting section;
   first receiving means for receiving and photoelectrically converting forward scattered light from said detecting section, and second receiving means for receiving and photoelectrically converting laterally scattered light from said detecting section;
   comparator means connected to said first receiving means for comparing a level of signal pulses of said forward scattered light with a predetermined threshold level and for generating of timing pulses from moments at which said signal pulses exceed said threshold level;
   pulse generating means connected to said comparator means for generating gate pulses by adding a predetermined period to said timing pulses;
   delaying means connected to said first and second receiving means for delaying a photoelectrically converted detecting signal of each of said forward and said laterally scattered light and for generating from each a delayed signal pulse;
   measuring means for measuring values, by a selected one of integrating and peak-holding, of each delayed signal pulse outputted from said delaying means during the period of said gate pulses; and
   analyzing means for analyzing the particles using the values of each delayed signal pulse measured by said measuring means.

7. An apparatus according to claim 6, wherein said second receiving means comprises plural light detectors for separately receiving the lateral scattered light and fluorescent light.

8. An apparatus according to claim 6, wherein said detecting section is a flow passage in a flow cell and each particle passes one by one through the detecting section.

9. An apparatus according to claim 6, wherein said irradiation means comprises a laser source.

* * * * *

UNITED STATES PATENT AND TRADEMARK OFFICE
CERTIFICATE OF CORRECTION

PATENT NO. : 4,986,657
DATED : January 22, 1991
INVENTOR(S) : SHINICHI OHE

It is certified that error appears in the above-identified patent and that said Letters Patent is hereby corrected as shown below:

COLUMN 1

Line 19, "as" should be deleted.
Line 41, "to peak" should read --to a peak--.
Line 55, "the integration" should read --integration--.

COLUMN 2

Lines 10-11, lines 10 and 11 should be deleted.
Line 14, "passes" should read --passed--.

COLUMN 3

Line 9, "present" should read --prevent--.
Line 23, "dyes" should read --dyed--.
Line 57, "circuit 8." should read --circuits 8.--.
Line 62, "sectional" should read --section--.

COLUMN 4

Line 1, "circuit 8" should read --circuits 8--.
Line 43, "value q" should read --value g--.

UNITED STATES PATENT AND TRADEMARK OFFICE
CERTIFICATE OF CORRECTION

PATENT NO. : 4,986,657

DATED : January 22, 1991

INVENTOR(S) : SHINICHI OHE

It is certified that error appears in the above-identified patent and that said Letters Patent is hereby corrected as shown below:

COLUMN 6

Line 45, "lateral" should read --laterally--.

Signed and Sealed this

Twenty-ninth Day of December, 1992

Attest:

DOUGLAS B. COMER

Attesting Officer        Acting Commissioner of Patents and Trademarks